United States Patent
Agrawal et al.

(10) Patent No.: US 7,878,993 B2
(45) Date of Patent: Feb. 1, 2011

(54) ANKLE-FOOT ORTHOSIS DEVICE

(75) Inventors: Sunil K. Agrawal, Newark, DE (US); Abhishek Agrawal, Ann Arbor, MI (US); Sai Banala, Newark, DE (US); Stuart Binder-MacLeod, Newark, DE (US)

(73) Assignee: University of Delaware, Newark, DE (US)

( * ) Notice: Subject to any disclaimer, the term of this patent is extended or adjusted under 35 U.S.C. 154(b) by 1005 days.

(21) Appl. No.: 11/453,386

(22) Filed: Jun. 15, 2006

(65) Prior Publication Data

US 2007/0049858 A1 Mar. 1, 2007

Related U.S. Application Data

(60) Provisional application No. 60/690,857, filed on Jun. 15, 2005.

(51) Int. Cl.
- A61H 1/00 (2006.01)
- A61H 1/02 (2006.01)
- A61H 5/00 (2006.01)
- A61F 5/00 (2006.01)

(52) U.S. Cl. .................. 601/27; 601/5; 602/27
(58) Field of Classification Search ............. 601/5, 601/27, 29, 31–35; 602/23, 27–29
See application file for complete search history.

(56) References Cited

U.S. PATENT DOCUMENTS

| | | | |
|---|---|---|---|
| 246,984 A | | 9/1881 | Stillman |
| 5,170,776 A | * | 12/1992 | Pecheux .................. 601/29 |
| 5,215,508 A | * | 6/1993 | Bastow .................... 482/79 |
| 5,335,674 A | * | 8/1994 | Siegler .................... 600/595 |
| 5,352,185 A | * | 10/1994 | Blauth et al. ............. 601/32 |
| 5,370,604 A | | 12/1994 | Bernardoni |
| 5,583,407 A | * | 12/1996 | Yamaguchi .............. 318/551 |
| 5,775,332 A | | 7/1998 | Goldman |
| 6,860,864 B2 | | 3/2005 | Meyer |

(Continued)

OTHER PUBLICATIONS

Ferris, Daniel P., et al. "An Ankle-Foot Orthosis Powered By Artificial Muscles"; available at www.asbweb.org/conferences/2001/2001.html; 2 Pages.

Blaya, Joaquin A., et al. "Adaptive Control of a Variable-Impedance Ankle-Foot Orthosis to Assist Drop-Foot Gait"; IEEE Transactions of Nural Systems and Rehabilitation Engineering, vol. 12, No. 1, Mar. 2004; pp. 24-31.

(Continued)

Primary Examiner—Steven O Douglas
Assistant Examiner—Kristen C Matter
(74) Attorney, Agent, or Firm—McCarter & English (57) ABSTRACT

An ankle-foot orthosis comprising a leg member 12; a foot member 14; a frame 16 connecting the leg member to the foot member, wherein the frame comprises a first revolute joint 18 that rotates about a first axis 20 and a second revolute joint 22 that rotates about a second axis 24, wherein the first and second axes are non-parallel. The frame can further comprise a foot member segment 30 secured to the foot member 14 and extending to the second revolute joint 22. The orthosis can comprise a first force-torque sensor 36 located on the leg member, a second force-torque sensor 38 located on the foot member, and an encoder positioned on one of the revolute joints. The invention includes a method of measuring ankle-foot-related forces comprising positioning a subject's leg and foot in an ankle-foot orthosis; collecting data from the first and second force-torque sensors; and analyzing the collected data to determine the motion of the subject's ankle.

20 Claims, 10 Drawing Sheets

U.S. PATENT DOCUMENTS

| | | |
|---|---|---|
| 6,887,213 B2 | 5/2005 | Smits |
| 6,926,687 B2 | 8/2005 | Shields |
| 7,018,350 B2 | 3/2006 | Hinshon |
| 7,018,352 B2 | 3/2006 | Pressman et al. |
| 2006/0069336 A1* | 3/2006 | Krebs et al. ............... 602/28 |

OTHER PUBLICATIONS

Yamamoto, Sumiko; "Development of an Ankle-Foot Orthosis with Dorsiflexion Assist, Part 2: Structure and Evaluation"; IPO 1999; vol. 11, Num 2; pp. 1-8.

* cited by examiner

ANKLE-FOOT ORTHOSIS DEVICE

CROSS REFERENCE TO RELATED APPLICATIONS

This application claims the benefit of U.S. Provisional Application No. 60/690,857, filed Jun. 15, 2005, the contents of which are incorporated herein by reference.

RELATED FEDERALLY SPONSORED RESEARCH

The work described in this application was sponsored by the following Federal Agencies: NIH, grant number 1R01 HD38582-01A2.

FIELD OF THE INVENTION

The present invention is directed to an ankle-foot orthosis device. More particularly, the invention is directed to an improved ankle-foot orthosis device providing two degrees-of-freedom motion, specifically addressing both inversion-eversion and dorsiflexion-plantarflexion.

BACKGROUND OF THE INVENTION

An ankle-foot orthosis (AFO) is commonly used to help subjects with weakness of ankle dorsiflexor muscles due to peripheral or central nervous system disorders. Both of these disorders are due to the weakness of the tibialis anterior muscle which results in lack of dorsiflexion assist moment. The deformity and muscle weakness of one joint in the lower extremity influences the stability of the adjacent joints, thereby requiring compensatory adaptations.

During level ambulation, the ankle should be close to a neutral position (a right angle) each time the foot strikes the floor. Insufficient dorsiflexion may be the result of hyperactive plantarflexion muscles that produce a very high plantarflexion moment at the ankle, or weakness of the dorsiflexion muscles. This affects the ability of the ankle to dorsiflex. Both of these cause the patient to make a forefoot contact instead of the normal "heel-strike". If there is a weak push-off, the stride length reduces, and the gait velocity fails. Similarly, during the swing phase of the gait, the ankle is dorsiflexed to allow the foot to clear the ground while the extremity is advanced. Hyperactive or weak dorsiflexors may result in insufficient dorsiflexion, which must be compensated for by alterations in the gait patterns so that the toes do not drag. This insufficient dorsiflexion during the swing phase of the gait is termed as "foot-drop". In addition to the toes dragging, the foot may become abnormally supinated, which may result in an ankle sprain or fracture, when the weight is applied to the limb. Foot-drop is commonly seen in subjects who have had a stroke or who have sustained a personal nerve injury.

There are several possible treatments for foot-drop including medicinal, orthotic, or surgical interventions. Of these, orthotic treatment is the most common. Orthotic devices are intended to support the ankle, correct deformities, and prevent further occurrences. A key goal of orthotic treatment is to assist the patient in achieving a measure of normal function.

There are a number of commercially available ankle-foot orthoses. All, however, are single axis or elastically deformable. While inversion-eversion motion in all of these orthoses is accommodated through the flexibility of the material, such as polypropylene, the limitation in normal inversion-eversion does not provide a natural motion to the ankle and adds discomfort. Thus, there is a need for an ankle foot orthosis allowing for a more natural motion of the ankle during movement.

SUMMARY OF THE INVENTION

An ankle-foot orthosis comprising a leg member 12, a foot member 14, and a frame 16 connecting the leg member to the foot member. The frame comprises a first revolute joint 18 that rotates about a first axis 20 and a second revolute joint 22 that rotates about a second axis 24. The first and second axes are non-parallel. The frame can further comprise a foot member segment 30 secured to the foot member 14 and extending to the second revolute joint 22. The orthosis includes a first force-torque sensor 36 located on the leg member, a second force-torque sensor 38 located on the foot member, and an encoder positioned on one of the revolute joints. The invention includes a method of measuring ankle-foot-related forces comprising positioning a subject's leg and foot in an ankle-foot orthosis, collecting data from the first and second force-torque sensors, and analyzing the collected data to determine the motion of the subject's ankle.

DETAILED DESCRIPTION OF THE INVENTION

The present invention provides an ankle-foot orthosis device with two degrees-of-freedom. The two motions incorporated are dorsiflexion-plantarflexion and inversion-eversion. This orthosis is useful to assist subjects with weakness of ankle dorsiflexor muscles. It allows two degrees-of-freedom motion, i.e., dorsiflexion-plantarflexion and inversion-eversion motion, while serving to maintain proper foot position for subjects during gait.

Figure 1:
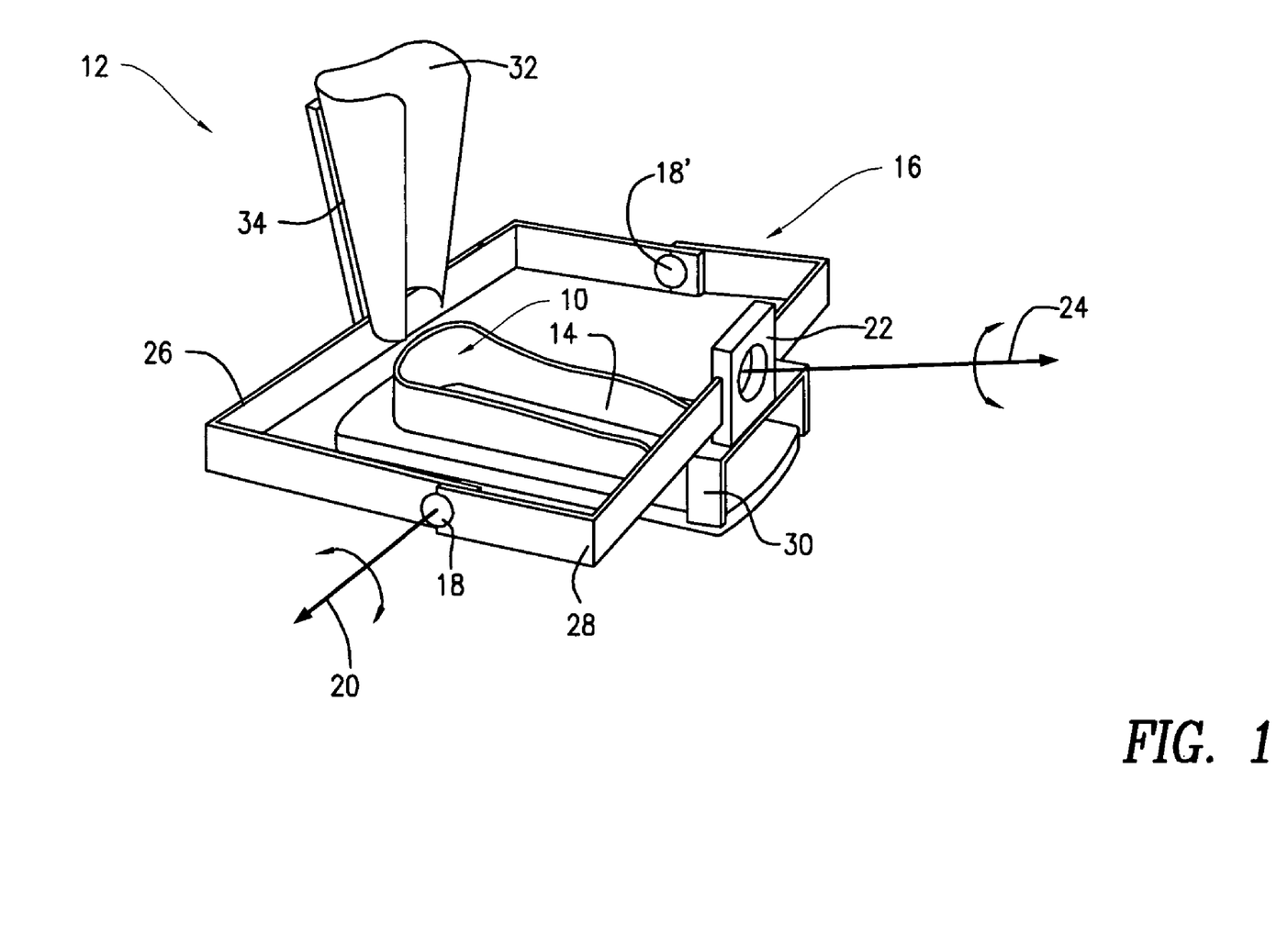
FIG. 1 is a schematic representation of an ankle-foot orthosis in accordance with one embodiment of the invention.

Referring to FIG. 1 which is a schematic of a device in accordance with the present invention, an ankle-foot orthosis 10 is shown as comprising a leg member 12, a foot member 14, and a frame 16 connecting the leg member to the foot member. The leg member is adapted to be secured to a patient's leg. A leg cradle 32 can be used to secure the device to a patient's leg. The leg cradle can then be secured to a leg support 34. Although not shown in FIG. 1, the leg member can be secured to the patient's leg by straps, tape, or other appropriate mechanism.

The foot member 14 can be adapted to fit the patient's foot, or a portion thereof. For both the leg cradle and the foot member, portions adapted to fit the patient can be custom manufactured to provide optimal patient comfort, or may be shaped generally to fit the legs and feet of many patients adequately.

The frame 16 comprises a first revolute joint 18 that rotates about a first axis 20. The first revolute joint correlates to the dorsiflexion-plantarflexion center of rotation in the human ankle. Motion along this axis occurs in the sagittal plane; the foot plantar flexes when it moves downwards away from the tibia, and dorsiflexes when it moves upwards toward the tibia. To facilitate symmetric motion, as shown in FIG. 1, the frame has duplicate first revolute joints (18 and 18') about the dorsilflexion-plantarflexion axis 20.

The position of the first rotational axis varies among users of different sizes and mobility. In one embodiment, the frame may be adjusted through a variety of mechanisms to locate the appropriate axis for a given user. One such mechanism is to assemble the frame using telescopic components to adjust the position of the axis, while keeping the orientation of the axis to the frame fixed. Alternatively, the position of the axis may be fixed, while the orientation relative to the patient's foot is adjustable.

The frame also comprises a second revolute joint 22 that rotates about a second axis 24. The first and second axes are non-parallel. The second revolute joint correlates to the inversion-eversion center of rotation in the human ankle. Motion along this axis occurs in the frontal plane; the foot inverts when it twists inwards and upwards, moving the sole towards the midline. The foot everts when it twists outwards and upwards, moving the sole away from the midline. While reference is made throughout this application to the inversion-eversion joint and axis, this degree of freedom may also be referred to as the pronation-supination axis or joint. Pronation and supination movements involve simultaneous movement in the frontal, sagittal, and transverse planes. Because it is clinically difficult to assess these triplane movements, the degree of motion about the inversion-eversion axis typically signifies the amount of protonation and supination. Accordingly, reference herein to the inversion-eversion motion encompasses protonation-supination motion in clinical assessment contexts.

The first and second revolute joints are connected in the frame through segments that can be rigid, adjustable, or malleable. Again referring to FIG. 1, the frame comprises a first segment 26 that is secured to the leg member 12 and extends to the first revolute joint 18. A second segment 28 connects the first and second revolute joints. The second segment 28 extending from the first revolute joint 18 to the second revolute joint 22. The second revolute joint 22 is connected to the foot member 14 by a foot member segment 30. The foot member segment 30 is secured to the foot member 14 and extends to the second revolute joint 22.

Figure 2:
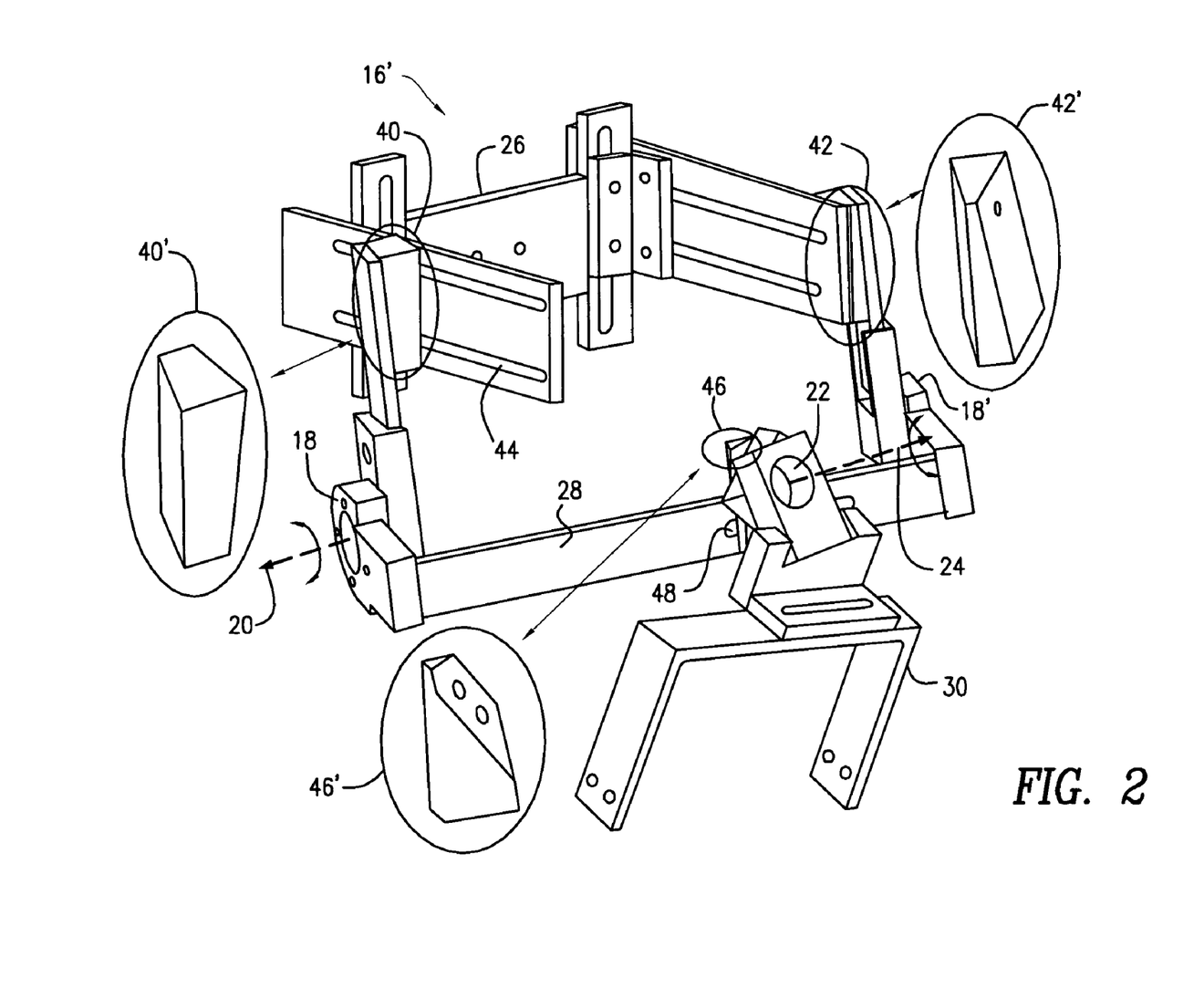
FIG. 2 is a 3D AutoCAD drawing of an ankle-foot orthosis in accordance with one embodiment of the invention.

Details of one embodiment of the frame 16' of the present invention is shown in FIG. 2. In this embodiment, the first rotational axis, that corresponding to the dorsilflexion-plantarflexion axis 20, is oriented through a combination of obliquely cut orientation components. A first orientation component 40 (enlarged as 40') and a second orientation component 42 (enlarged as 42') establish the orientation of the revolute joint axis 20 relative to the frame 16'. In this embodiment, positioning tracks 44 allow for the orientation components to move in position relative to the rest of the frame, permitting optimization of confluence between the patient's ankle movement and the orthosis available axis of rotation.

In one embodiment of the present invention, the second rotational axis 24, that corresponding to the inversion-eversion axis, is oriented through a single obliquely cut orientation component 46 (enlarged as 46'). While not as easily viewed in FIG. 2, a second revolute joint positioning track 48 allows the position of the revolute joint to be adjusted to correlate the rotational axis with the movement of the user.

By providing two degrees-of-freedom, the device allows ankle motion to be measured as a function of movement in both rotational axes. Measurement of the forces and torques applied by a user is useful in many applications. The collected data can be useful in diagnosing mobility disorders, identifying movement and gait attributes, such as protonation in gait, and assessing the nature and severity of injuries. The data can be used in conjunction with a kinematics model for the motion of the foot, as discussed in more detail in Example 1.

Figure 3:
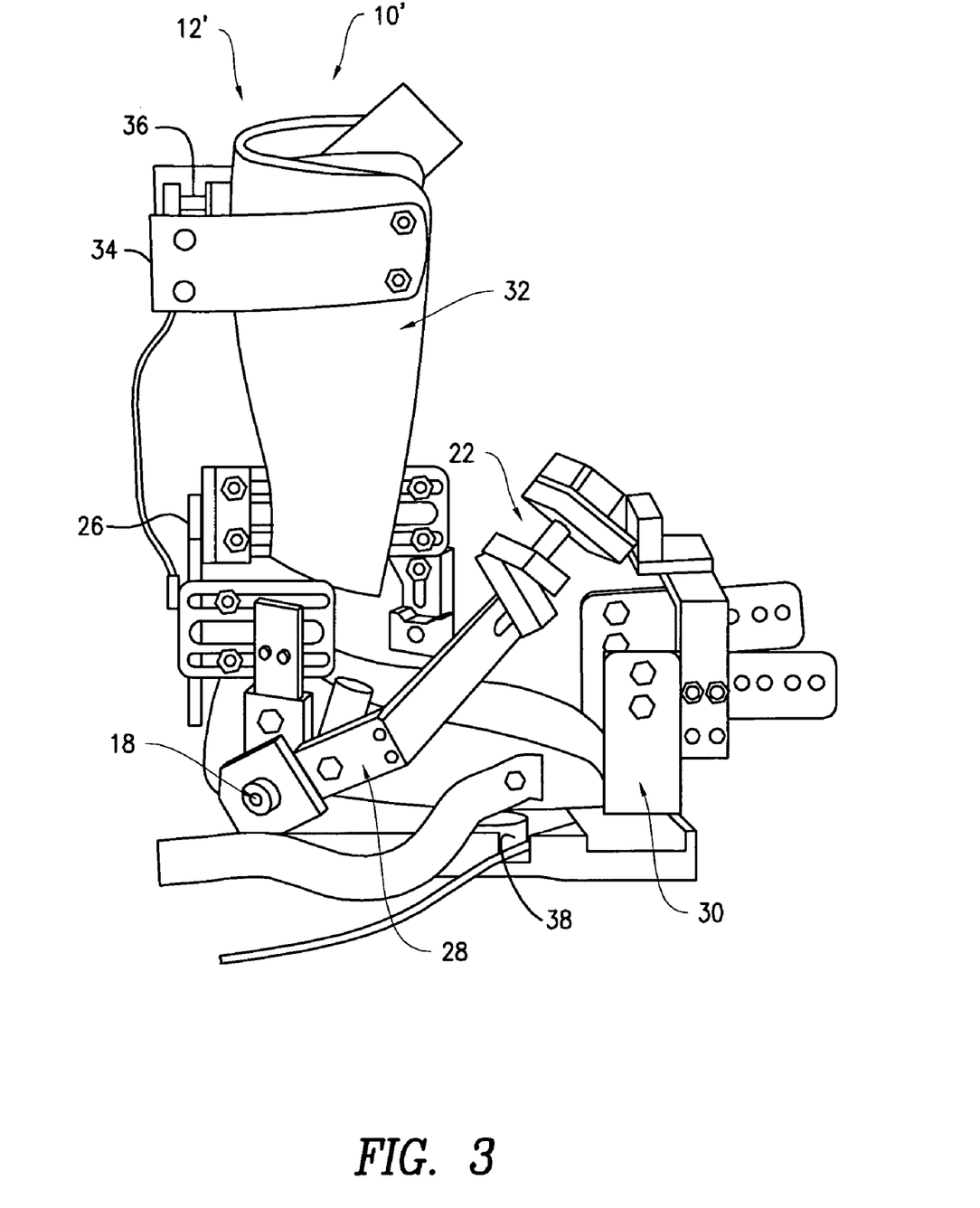
FIG. 3 is a representation of a side view of an ankle-foot orthosis in accordance with one embodiment of the invention.

The ankle-foot orthosis of the present invention can be equipped to collect force and torque data. In one embodiment, illustrated in FIG. 3, force-torque sensors are placed on the orthosis in positions that are compatible with providing data to an exemplary kinematics model. A first force-torque sensor 36 is located on the leg member. The leg member has a leg cradle 32 and a leg support 34, and the first force-torque sensor 36, in this embodiment, is located between the leg cradle and the leg support. A second force-torque sensor 38 is located on the foot member. As shown in FIG. 3, the second force-torque sensor is located in a position below the sole of the user's foot.

Standard, commercially available force torque sensors can be used to collect the force and torque applied in locations around the orthosis of the invention. As explained in Example 1, the positions of the force-torque sensors on the leg member and beneath the sole of the foot on the foot member are appropriate for collecting data for use with a kinematics model that includes two-degrees-of-freedom. Other positions, or additional points of data may be appropriate for use with the device when employing an alternate kinematics model for data analysis.

Appropriate commercially available force-torque sensors include the ATI Force Torque Sensor Mini45 model available from ATI Industrial Automation and the JR3 Force Torque Sensor 67M25S-M40B-A 135L350 model from JR3, although any sensor providing sufficiently precise force and torque data can be used.

Figure 4:
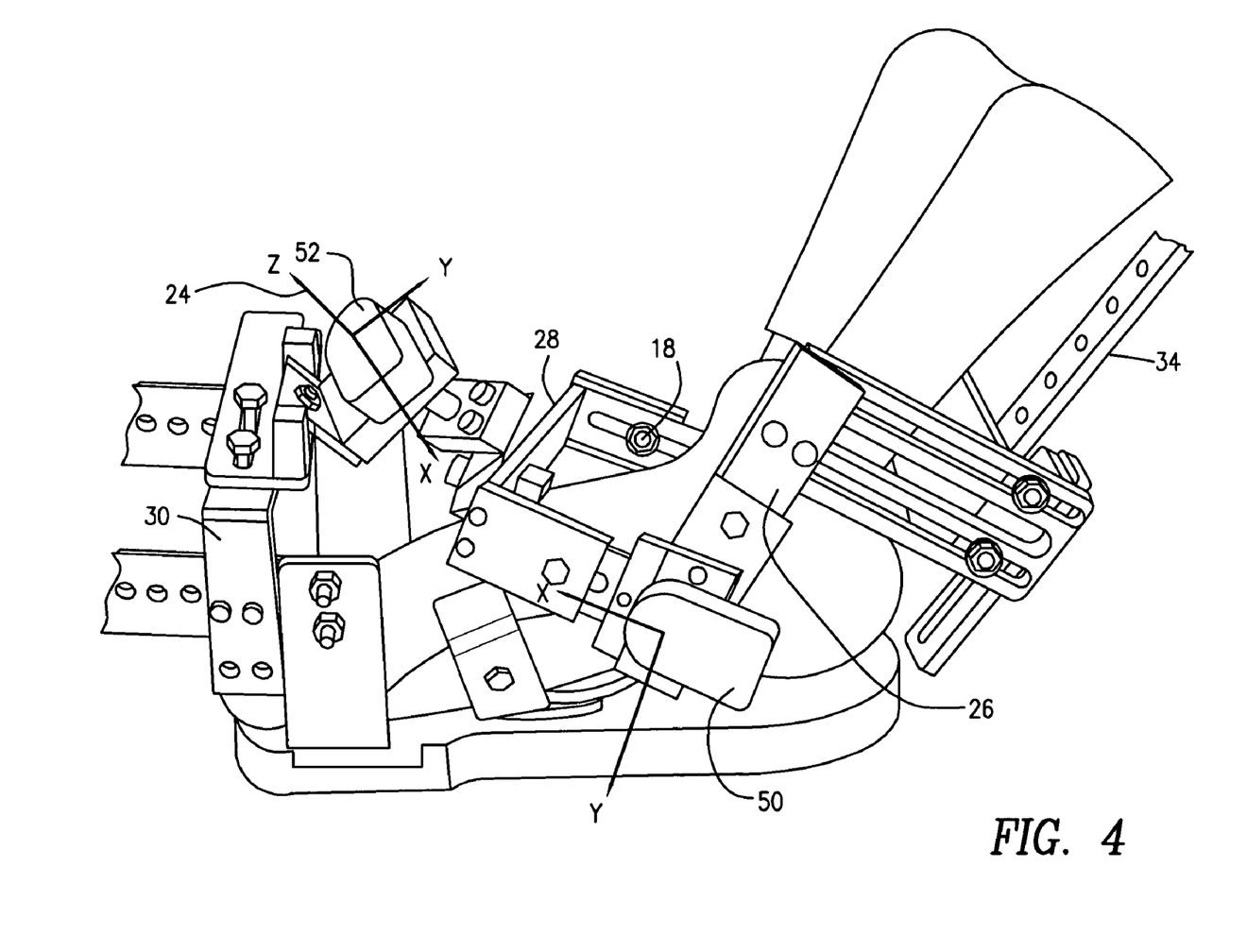
FIG. 4 is a representation of a side view of an ankle-foot orthosis in accordance with one embodiment of the invention.

Additionally, data can be collected at the revolute joints via encoders. Encoders produce outputs which indicate the speed, angle, and direction of the rotational shaft in a joint. With reference to FIG. 4, encoders are shown positioned to record speed, angle, and directional information from the first and second revolute joints. The first encoder 50 is positioned to record data from the first revolute joint, while the second encoder 52 is positioned to record data from the second revolute joint. Depending on the application and kinematics model employed, a single encoder or multiple encoders can be used in conjunction with the orthosis.

Figure 5:
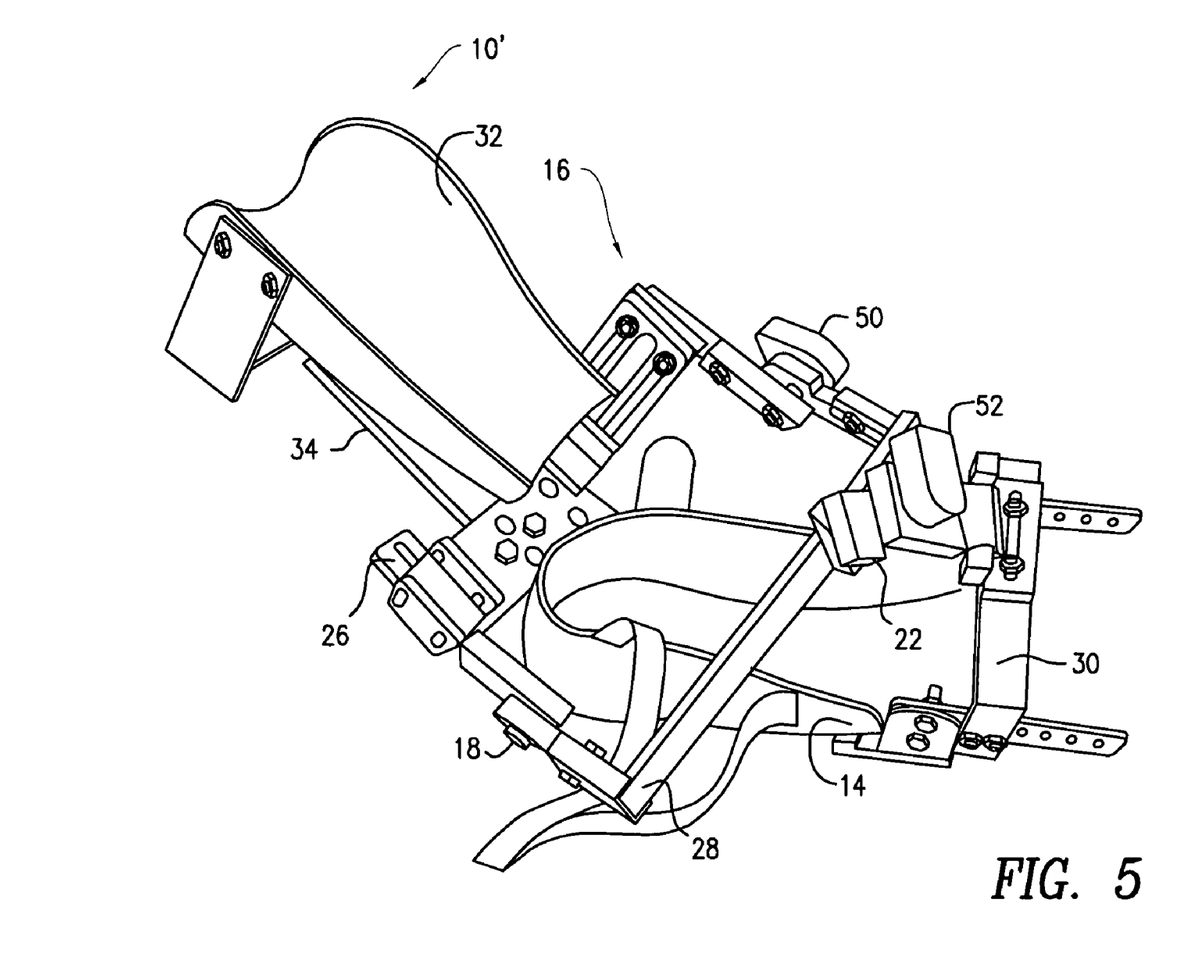
FIG. 5 is a representation of a top view of an ankle-foot orthosis in accordance with one embodiment of the invention.

Referring to FIG. 5, the same device as that shown in FIGS. 3 and 4, is shown in an open configuration. Here, the positions of the encoders 50, 52 are apparent relative to the segments of the frame and the leg and foot members.

In addition to diagnostic and research applications of the orthosis of the invention, the orthosis can be used in conjunction with control mechanisms to provide mechanical assistance to the user and serve as a therapy aid or an ambulatory aid. In one embodiment, the ankle-foot orthosis of the invention comprises a means for controlling one of the revolute joints, such as a motor. Also, springs or other actuators can be used to impart forces on the joints. The amount of the force exerted by a motor or other device can be adjusted in view of data collected through force-torque sensors, encoders, or other devices. The adjustment may occur in real time as the user moves. Alternatively, the motor, spring, or other device imparting forces on the joints may be calibrated in view of measurements collected for a particular users.

Measuring the ankle-foot-related forces in accordance with the invention includes positioning a subject's leg and foot in the ankle-foot orthosis. As discussed above, various options exist for securing the leg and foot to the orthosis, with hook and loop straps as an example shown in FIGS. 4 and 5. Data is collected from the first and second force-torque sensors positioned at the first and second revolute joints and these collected data are analyzed using a kinematics model for the motion of the foot to determine the forces involved in the movement of the subject's ankle.

Additionally, depending on the kinematics model employed, data from an encoder, or multiple encoders can be collected and analyzed in determining the forces and features of the motion of the subject's ankle.

Ankle-mobility disorders can be treated using the orthosis by using the measured data from the orthosis to manipulate and adjust motors and other devices that can control the subject's foot motion, or exert forces to aide in achieving proper motion. Similarly, a corrective orthosis may be designed by using the collected and analyzed data from the orthosis sensors and encoders and using the resulting profile of the user's gaits to providing means to compensate for a joint force deficiency identified by the data analysis. Ideally, the means to compensate are proportional to the joint force deficiency, or otherwise optimized to correct for the deficiency of a particular user. The means for compensating can include springs, motors and other actuators.

The orthosis can also be an integral part of another rehabilitation device. In any application, the position of the leg in the gait cycle is available at all times, and the motion of the ankle can be controlled accurately.

EXAMPLES

Example 1

Kinematics Model for Ankle-Foot Motion

In this example, the motion of the ankle is modeled based on two degrees-of-freedom. The first degree-of-freedom is a rotation in the vertical plane about an axis ($Z_1$) passing through the ankle joint. This axis is known as the dorsiflexion-plantarflexion (D/P) motion axis. The second degree-of-freedom is a rotation about an axis ($Z_2$). This motion is known as inversion-eversion (I/E) motion. For this model, segments of the foot are assumed to be rigid links, and the dorsiflexion-plantarflexion and inversion-eversion motions are approximated by revolute joints.

Figure 6:
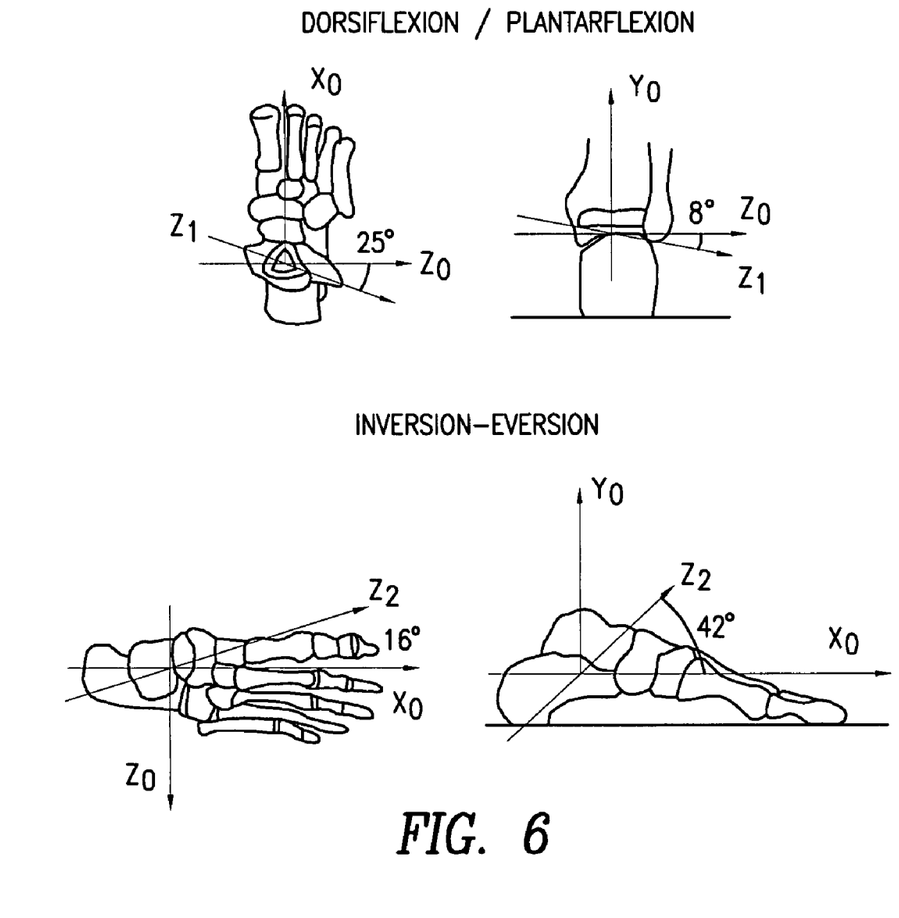
FIG. 6 is a diagram showing various orientations of dorsiflexion-plantarflexion joint axis $Z_1$ and inversion-eversion joint axis $Z_2$ in relation to the ankle and foot.

The orientations of the two joint axes considered in this study are shown in FIG. 6, which shows the projection of the joint axes in the frame attached to the leg shank ($X_0, Y_0, Z_0$). The axis $Z_0$ represents the knee joint axis. This projection is taken when the foot is resting firmly on the ground and the leg is perpendicular to the ground.

The Denavit-Hartenberg (DH) parameters of the kinematic model as described with reference to in FIG. 6 were determined, and the average lengths of the ankle-foot components were obtained from anthropomorphic data. The unit vectors $Z_1$ and $Z_2$ in the frame $Z_0$ were determined using the following relationship between spherical and Cartesian coordinates:

$x = r \cos \gamma \sin \phi$, $y = r \sin \gamma \cos \phi$, $z = r \cos \phi$

Because the projections $\vec{Z_1}$ and $\vec{Z_2}$ in $\vec{Z_0}$ are known empirically, the spherical coordinates can be computed, with values $\gamma_1 = 196.7°$, $\phi_1 = 25.9°$ for $Z_1$ and $\gamma_2 = 42°$, $\phi_2 = 102.0°$ for $Z_2$.

Subsequently, $\vec{X_1}$, $\vec{Y_1}$ axes and $\vec{X_2}$, $\vec{Y_2}$ axes are defined as follows:

$$\vec{X}_{i+1} = \frac{\vec{Z}_i \times \vec{Z}_{i+1}}{\left\| \vec{Z}_i \times \vec{Z}_{i+1} \right\|}$$

$$\vec{Y}_{i+1} = \frac{\vec{Z}_{i+1} \times \vec{X}_{i+1}}{\left\| \vec{Z}_{i+1} \times \vec{X}_{i+1} \right\|}.$$

The Denavit-Hartenberg parameters $\theta_i$, $\alpha_i$, $a_1$, and $d_1$ were used to locate the frames on the bodies. Once all the unit vectors $\vec{X}_i$, $\vec{Y}_i$ and $\vec{Z}_i$ are known, $\theta_i$ and $\alpha_i$ are computed using vector algebra. $a_i$ and $d_i$ were computed using anthropomorphic data and loop closure equation, $T_0^3 = T_0^1 T_1^2 T_2^3$, where $T_i^{i+1}$ denotes the transformation matrix between two successive bodies i and i+1. In the nominal configuration of the foot, when the foot is flat on the ground and perpendicular to the leg shank, the DH parameters computed are:

$T_0^1, \theta_0 = 286.7°$ and $\alpha_0 = 25.9°$ $T_1^2, \theta_1 = 210.6°$ and $\alpha_1 = 125.0°$ $T_2^3, \theta_2 = 13.1°$ and $\alpha_2 = 0°$ $\theta_i$ are the joint variables, which take the particular values shown above for the mentioned configuration of the foot. With these parameters calculated, the complete kinematics model is established.

Example 2

Measuring Forces and Torques Applied at the Dorsalflexion-Plantarflexion and Inversion-Eversion Joints In measuring the forces and torques at the revolute joints of the orthosis, a Newton-Euler analysis can be used to convert the raw force-torque sensor and encoder data into joint forces and torques. When using telescopic joints on the orthosis, the device can be adjusted to allow the axes of the device to coincide with the axes of the human motion. The device then moves largely synchronously with little or no relative motion compared to the subject's ankle and foot. The device can be adjusted until the subject is able to execute the normal motion of the foot. Perfect alignment between the human and device axes can be difficult, but there are several techniques to facilitate adequate agreement. The device and the subject's ankle and foot are kept largely fixed.

Figure 7:
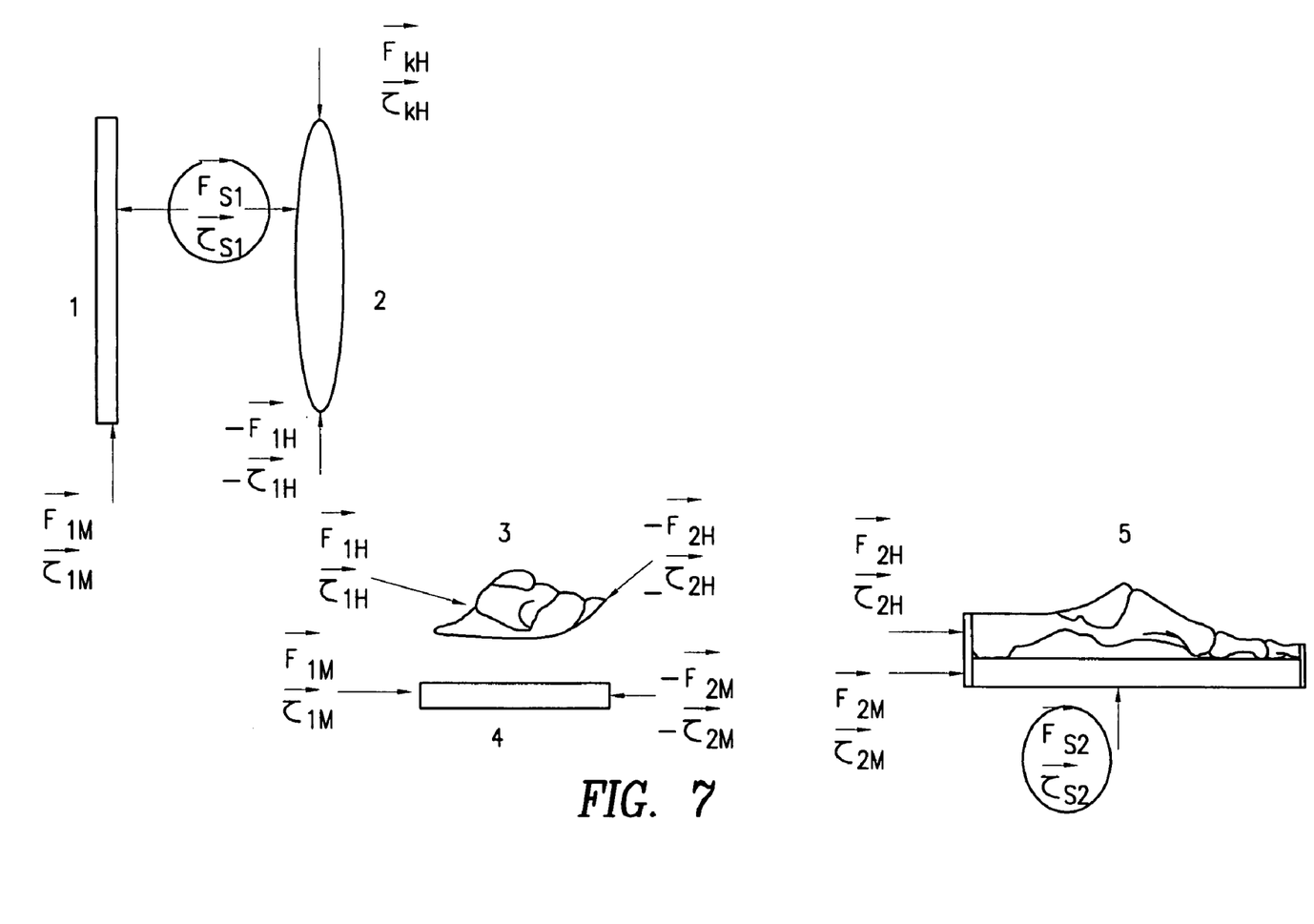
FIG. 7 is a free body diagram of the human and machine components relevant to one exemplary kinematics model.

The free body diagram shown in FIG. 7 illustrates five bodies contributing to this kinematics model. The first and the second bodies in FIG. 7 represent the device and the human leg shank, which are rigidly attached to each other and are inertially fixed. The third and fourth bodies represent the second segments of the subject's ankle and the corresponding segment of the device. The ankle is not in direct contact to the device in this area, but the orthosis provides that these segments move together as a rigid body. The third segment of the device and subject's foot are rigidly connected, and they collectively form the fifth body. The forces between these segments are shown in FIG. 7. The subscripts M and H signify the machine and the human components respectively and S implies the sensor component.

$\vec{F}_{1M}$, $\vec{\tau}_{1M}$ and $\vec{F}_{2M}$, $\vec{\tau}_{2M}$ are the forces and torques between the first-second and second-third links of the device at the dorsalflexion/plantarflexion (D/P) and inversion/eversion (I/E) joints respectively.

$\vec{F}_{1H}$, $\vec{\tau}_{1H}$ and $\vec{F}_{2H}$, $\vec{\tau}_{2H}$ are the forces and torques in between the segments of the human lower leg at the D/P and I/E joints, respectively. The gravitational force is acting at the center of mass of each body and is not shown in the figure for the sake of clarity.

$\vec{F}_{kH}$, $\vec{\tau}_{kH}$ are the force and the torque at the knee joint. Each of the bodies shown in FIG. 7 has a coordinate frame attached to it. The encoder data along with the geometric details of the device are used to calculate the translational and rotational velocities and accelerations of each of the bodies. Moment balance about the body center of mass and force balance equations are written for each body in its body coordinate frame. All forces and moments are three dimensional. Each body has two vector equations, i.e., six scalar equations. There are five bodies, so there is a total of thirty equations.

The vector unknowns are $\vec{F}_{1M}$, $\vec{\tau}_{1M}$, $\vec{F}_{2M}$, $\vec{\tau}_{2M}$, $\vec{F}_{1H}$, $\vec{\tau}_{1H}$, $\vec{F}_{2H}$, $\vec{\tau}_{2H}$, $\vec{F}_{kH}$ and $\vec{\tau}_{kH}$ so there are thirty scalar unknowns. The system is uniquely solvable. Solving the force and moment balance equations for the bodies one through five in the order 1-4-5-3-2 gives all the unknown forces and moments without any matrix inversions or iterative procedures. The force due to previous body on the next body is taken as positive and is expressed in the reference frame of the next body. The position vectors and gravity force of a particular body are expressed in the body frame.

Frame 0 is fitted to bodies 1 and 2; bodies 3 and 4 move together, so their coordinate frame have same orientations but different origins. These frames are represented by the same index 1 for the purpose of rotation matrices and finally frame 2 is attached to body 5. Bodies 3 and 4 have the same angular velocity and acceleration $\vec{\omega}_1$ and $\vec{\alpha}_1$, respectively. Body five has angular velocity and acceleration, $\vec{\omega}_2$ and $\vec{\alpha}_2$, respectively. The vector $\vec{r}_{1M;1}$ represents a vector from the D/P joint to the center of mass of body 1. Other position vectors follow similarly. The vector $\vec{F}_w$ represents the weight vector of respective bodies. Weights of the various human segments are obtained from the average anthropological data.

The force and moment balance equations for different bodies can be written as follows:

For body 1:

$$-\vec{F}_{s1} + \vec{F}_{w1} - R_0^1 \vec{F}_{1M} = \vec{0}, -\vec{\tau}_{s1} - R_0^1 \vec{\tau}_{1M} +$$
$$\vec{F}_{S1} \times \vec{r}_{S1;1} + (R_0^1 \vec{F}_{1M}) \times \vec{r}_{1M;1}$$
$$= \vec{0},$$

-continued

For body 4:

$$\vec{F}_{w4} - R_1^2 \vec{F}_{2M} - \vec{F}_{1M} = M_4 \vec{a}_{c4}, -R_1^2 \vec{\tau}_{2M} + \vec{\tau}_{1M} - (R_1^2 \vec{F}_{2M}) \times$$
$$\vec{r}_{2M;4} + \vec{F}_{1M} \times \vec{r}_{1M;4}$$
$$= I_4 \vec{\alpha}_1 + \vec{\omega}_1 \times I_4 \vec{\omega}_1,$$

For body 5:

$$\vec{F}_{S2} + \vec{F}_{w5} + \vec{F}_{2M} + \vec{F}_{2H} = M_5 \vec{a}_{c5}, \vec{\tau}_{S2} + \vec{\tau}_{2M} + \vec{\tau}_{2H} + \vec{F}_{S2} \times$$
$$\vec{r}_{S2;5} + \vec{F}_{2M;5} \times \vec{r}_{2M;5} \vec{F}_{2H;5} \times \vec{r}_{2H;5}$$
$$= I_5 \vec{\alpha}_2 + \vec{\omega}_2 \times I_5 \vec{\omega}_2,$$

For body 3:

$$\vec{F}_{w3} - R_1^2 \vec{F}_{2H} + \vec{F}_{1H} = M_3 \vec{a}_{c3}, -R_1^2 \vec{\tau}_{2H} + \vec{\tau}_{1H} - (R_1^2 \vec{F}_{2H}) \times$$
$$\vec{r}_{2H;3} + \vec{F}_{1H} \times \vec{r}_{1H;3}$$
$$= I_3 \vec{\alpha}_1 + \vec{\omega}_1 \times I_3 \vec{\omega}_1,$$

For body 2:

$$\vec{F}_{S1} + \vec{F}_{w2} - R_0^1 \vec{F}_{1H} + \vec{F}_{kH} = M_2 \vec{a}_{c2}, \vec{\tau}_{S1} - R_0^1 \vec{\tau}_{1H} + \vec{\tau}_{kH} + \vec{F}_{S1} \times$$
$$\vec{r}_{S1;2} - (R_0^1 \vec{F}_{1H}) \times \vec{r}_{1H;2} + \vec{r}_{kH;2} \times \vec{F}_{kH}$$
$$= I_2 \vec{\alpha}_0 + \vec{\omega}_0 \times I_2 \vec{\omega}_0,$$

The analysis presented in this section can be used to determine joint forces and moments for arbitrary motions of the ankle while the leg shank is inertially fixed. During walking, the shank is not inertially fixed and the rear foot experiences large ground reaction forces during heel strike. The orthosis can be used for walking experiments by adding a second force torque sensor between the rear foot and ground and by recording the motion information of the shank.

Example 3

Experimental Data Collected During Motion of the about the D/P Joint

Figure 8:
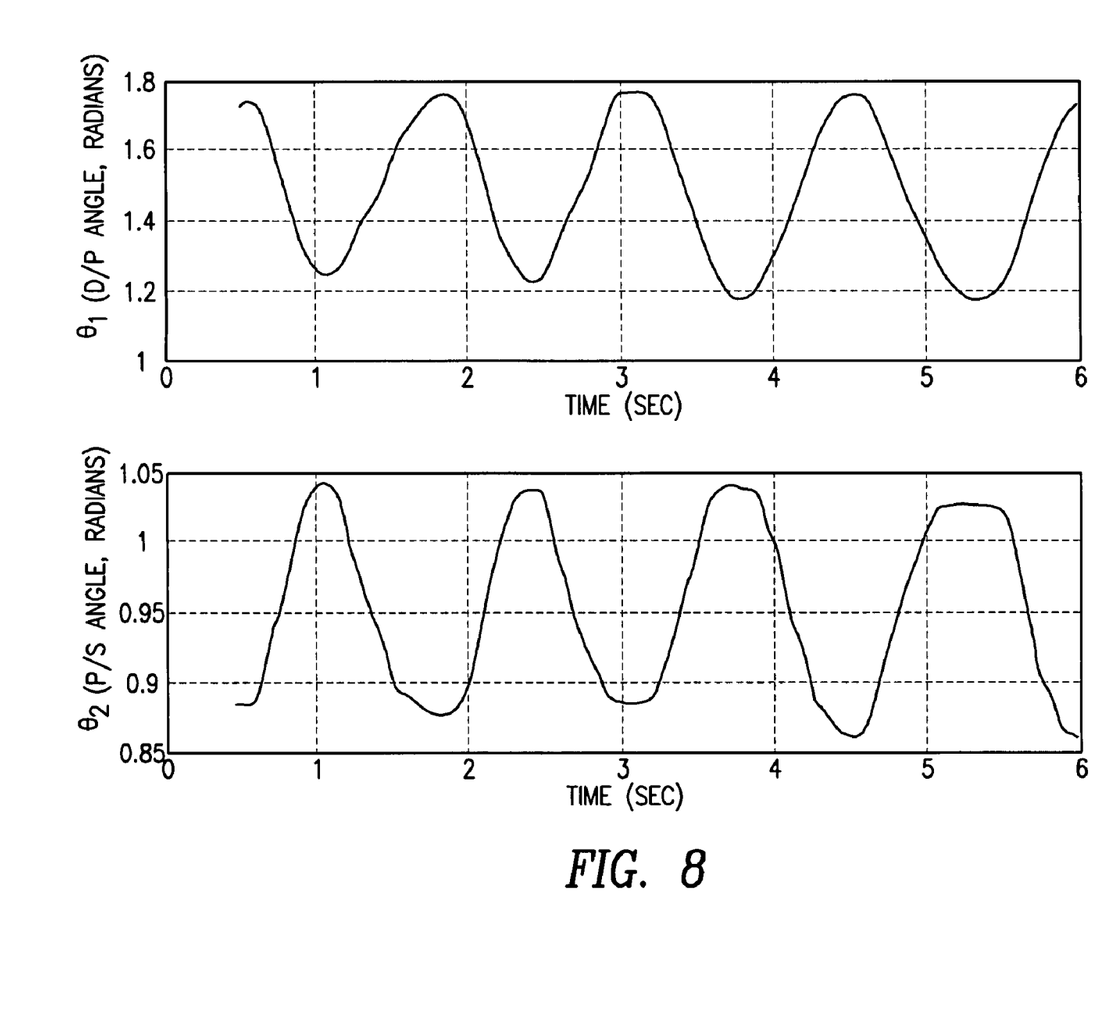
FIG. 8 provides two timeline graphs depicting joint rates over a period of time.
Figure 9:
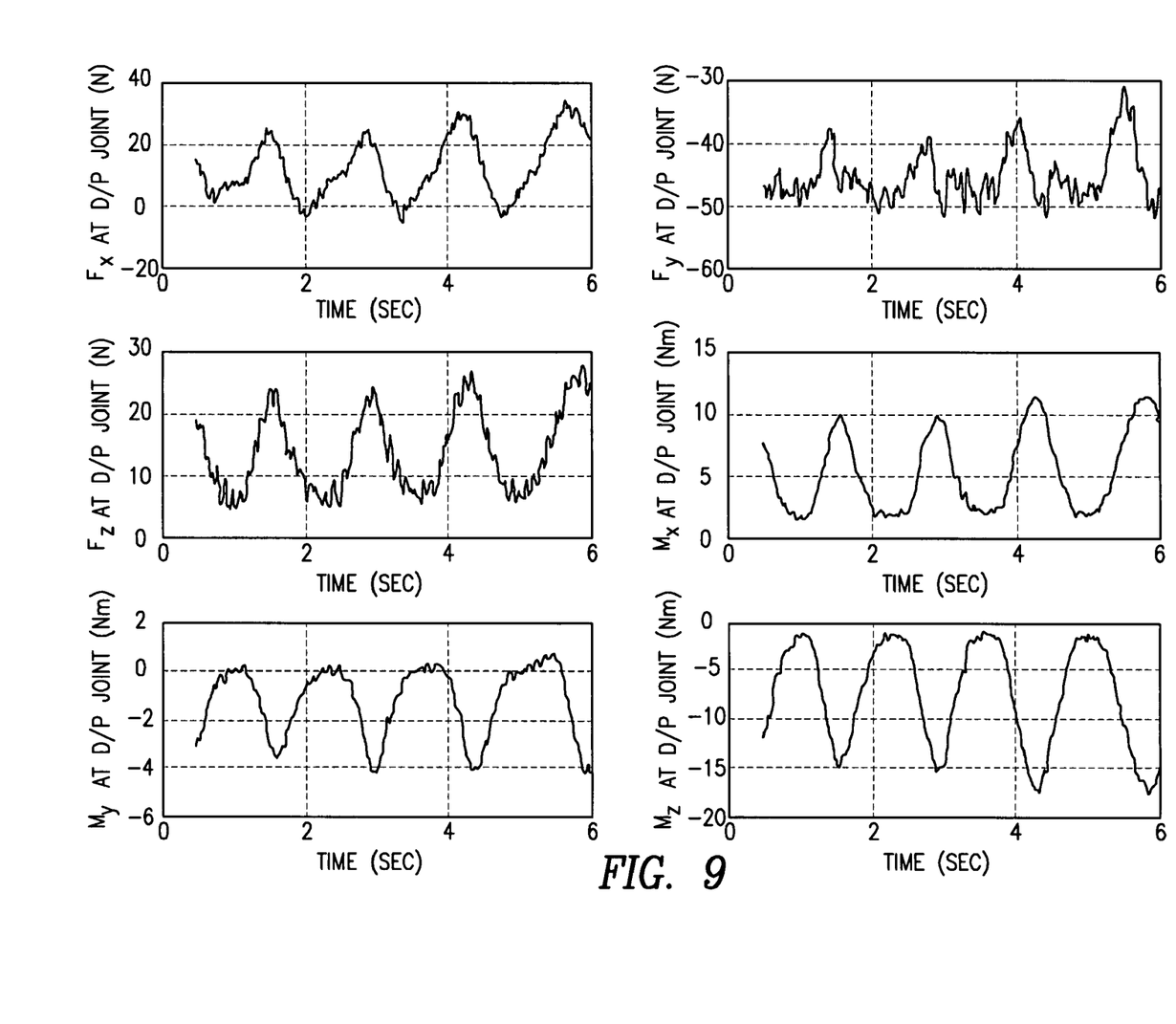
FIG. 9 are graphs displaying experimental data revealing the forces and moments about the dorsalflexion-plantarflexion joint during motion around the dorsalflexion-plantarflexion joint.
Figure 10:
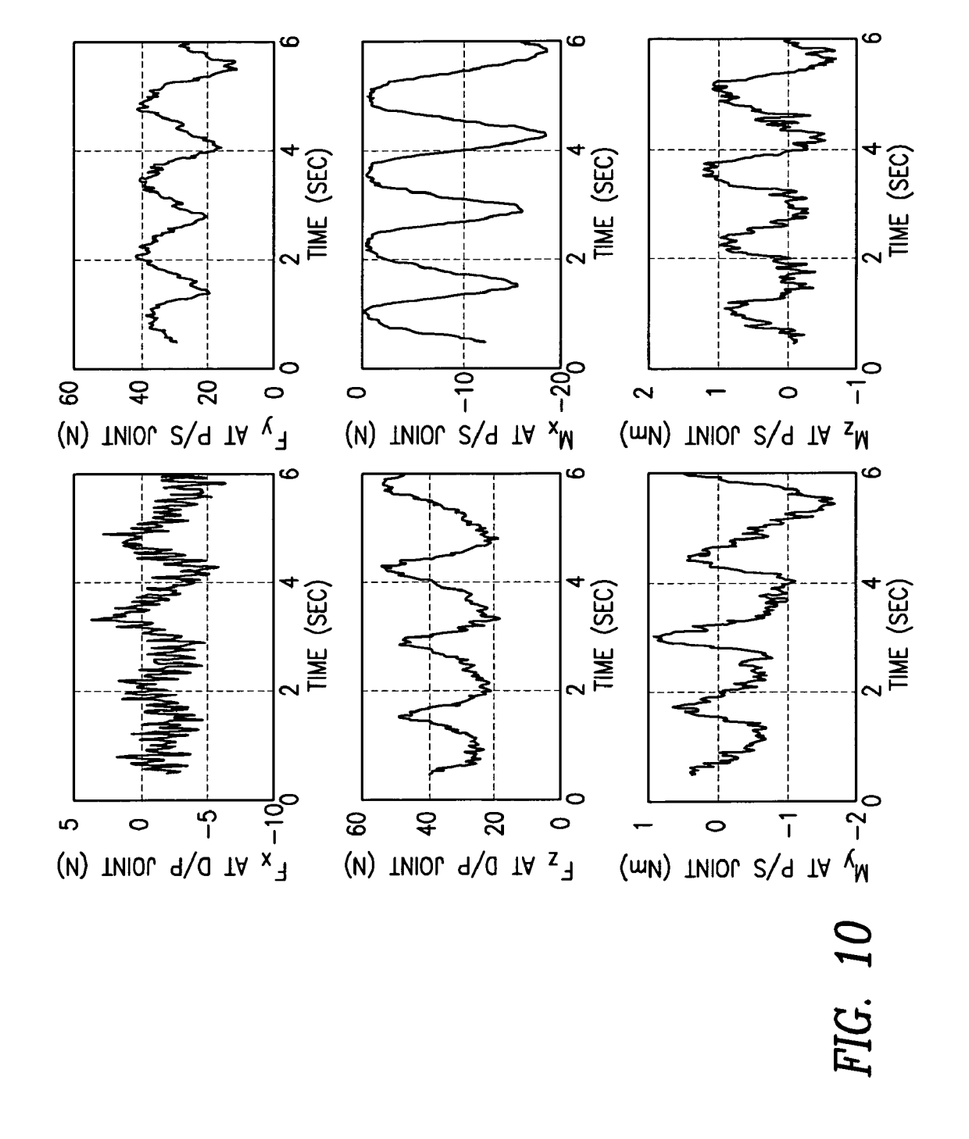
FIG. 10 are graphs displaying experimental data revealing the forces and moments about the inversion-eversion joint during motion about the dorsalflexion-plantarflexion joint.

Experimental results were obtained using a device in accordance with the present invention. Experiments were performed with a healthy subject who was asked to perform primarily motion about the D/P joint. Exemplary orientations of the D/P and I/E frames are shown in FIG. 4. The frames are placed at the actual joint in the human foot. The orientation information is useful in interpreting the collected data. The subject performed dorsiflexion-plantarflexion motion without contacting the foot to the ground. The ranges of rotation obtained are shown in FIG. 8. The range of motion during foot movement about the D/P axis was about 0.5 rad around the D/P axis and about 0.15 rad around the I/E axis. It can be seen that the frequency of motion is around 1 Hz, or one revolution of the joint per second. FIG. 9 presents the forces and torque applied by the subject about the D/P joint during the motion around the D/P axis. FIG. 10 presents the applied forces and torques about the I/E axis. Due to the periodic rotational motion about the axis, the forces and torques are also oscillatory about a mean. In FIG. 9, $M_z$ represents the torque about the D/P joint. The peak dorsiflexor torque is around 16 Nm and the peak plantarflexor torque is around 2 Nm.

The net torque applied by the shank to the foot at the D/P joint obtained by taking square root of the sum of squares of all the three components of moment, is about 8.5 Nm. The weight of foot is about 1 Kg and the weight of the relevant parts of orthosis is about 3 Kg, and the center of mass of the this weight is 20 cm from the D/P joint. This yields a torque of 8 Nm. Because there is some friction at the joints of the device the subject has to apply torques to overcome that as well, this explains the slightly higher magnitude of the experimental mean torque. From FIG. 4, we see that the X and Z axes are almost in the horizontal plane, thus the torques about these axes are relatively large as compared to the Y-axis. The direction of the Z axis is such that the shank has to apply a negative torque to balance the torque due to the weight of device and foot, consistent with the experimental data. The net force applied by the shank to the foot at the D/P joint is about 46 N. Because in this particular case, the total foot and device weight on the D/P joint is also about 4 Kg, the calculated force is about 40 N, which is about 6 N less than the mean of measured forces. This discrepancy can be attributed to friction. From FIG. 4, Y axis is pointing almost vertically downwards. Thus, the maximum force component of 43 N is about this axis and is negative because the shank has to apply an upwards force at this joint to balance the gravitation force. The other two components, though small compared to the Y component, should not be expected to be zero because none of the axes are perfectly in a vertical or horizontal plane. Similarly, FIG. 10 shows the forces and moments applied by the subject about the I/E joint during the movement of the foot around the D/P joint. The net moment about the I/E axis ($M_z$ in FIG. 10) has a mean of 0.3 Nm. This relatively small moment is consistent with the motion by the subject in only the D/P joint. Data collection and analysis was performed similarly while the subject moved the foot and ankle about the I/E axis.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An ankle-foot orthosis comprising:
    a leg member;
    a foot member, the foot member having: (i) a proximal end and a distal end, and (ii) a top side and a bottom side;
    a frame connecting the leg member to the distal end and top side of the foot member, the frame including:
        (i) a first frame segment secured to the leg member and extending from the leg member to a first and a second revolute joint, the first and second revolute joints configured and dimensioned to rotate about a first axis, and
        ii) a second frame segment extending from the first and second revolute joints to a third revolute joint, the third revolute joint being positioned: (i) at the distal end of the foot member, and (ii) on the top side of the foot member, the third revolute joint configured and dimensioned to rotate about a second axis, the second axis non-parallel to the first axis;
    wherein rotation of the first and second revolute joints about the first axis allows the first and second frame segments to rotate with respect to one another.

2. The ankle-foot orthosis of claim 1 wherein the frame further comprises first and second orientation components, the first and second orientation components configured and dimensioned to establish the orientation of the first axis relative to the frame.

3. The orthosis of claim 2, wherein the frame further includes a first positioning track and a second positioning track;
    wherein the first positioning track is configured and dimensioned to allow the first orientation component to move within the first positioning track relative to the frame to establish the orientation of the first axis relative to the frame; and
    wherein the second positioning track is configured and dimensioned to allow the second orientation component to move within the second positioning track relative to the frame to establish the orientation of the first axis relative to the frame.

4. The ankle-foot orthosis of claim 1 wherein the frame further comprises a orientation component, the orientation component configured and dimensioned to adjust the position of the third revolute joint to correlate the second axis with the movement of a user.

5. The orthosis of claim 4, wherein the frame further includes a positioning track, the positioning track configured and dimensioned to allow the orientation component to move within the positioning track to adjust the position of the third revolute joint to correlate the second axis with the movement of the user.

6. The ankle-foot orthosis of claim 1 wherein the frame further comprises a foot member segment secured to the distal end of the foot member and extending to the third revolute joint.

7. The ankle-foot orthosis of claim 1 further comprising a first force-torque sensor located on the leg member.

8. The ankle-foot orthosis of claim 7 wherein the leg member comprises a leg cradle and a leg support, the first force-torque sensor being located between the leg cradle and the leg support.

9. The ankle-foot orthosis of claim 7 further comprising a second force-torque sensor located on the foot member.

10. The ankle-foot orthosis of claim 1 further comprising an encoder positioned on one of the revolute joints.

11. The ankle-foot orthosis of claim 10 wherein the encoder measures the rotation of the first or second revolute joint.

12. The ankle-foot orthosis of claim 10 wherein the encoder measures the rotation of the third revolute joint.

13. The ankle-foot orthosis of claim 1 further comprising a means for controlling one of the revolute joints.

14. An ankle-foot orthosis comprising:
    a leg member;
    a foot member, the foot member having: (i) a proximal end and a distal end, and (ii) a top side and a bottom side;
    a frame connecting the leg member to the distal end and top side of the foot member, the frame including:
        (i) a first frame segment secured to the leg member and extending from the leg member to a first and a second revolute joint, the first and second revolute joints configured and dimensioned to rotate about a first axis,
        ii) a second frame segment extending from the first and second revolute joints to a third revolute joint, the third revolute joint being positioned: (i) at the distal end of the foot member, and (ii) on the top side of the foot member, the third revolute joint configured and dimensioned to rotate about a second axis, the second axis non-parallel to the first axis, and (iii) a foot member segment secured to the distal end of the foot member and extending to the third revolute joint;

a first force-torque sensor located on the leg member, a second force-torque sensor located on the foot member, and an encoder positioned on one of the revolute joints; and wherein rotation of the first and second revolute joints about the first axis allows the first and second frame segments to rotate with respect to one another.

15. The ankle-foot orthosis of claim 14 further comprising a first actuator positioned to control the frame motion about the first axis.

16. A method of measuring ankle-foot-related forces comprising:

positioning a subject's leg and foot in the ankle-foot orthosis of claim 14;

collecting data from the first and second force-torque sensors; and analyzing the collected data to determine the motion of the subject's ankle.

17. The method of claim 16 further comprising collecting data from the encoder, and analyzing the collected encoder data to determine the motion of the subject's ankle.

18. A method of treating ankle-mobility disorders comprising:

positioning a subject's leg and foot in the ankle-foot orthosis of claim 15;

collecting data from the first and second force-torque sensors;

analyzing the collected data to determine ankle-related forces; and manipulating the first actuator to control the subject's foot motion about the first axis.

19. A method of designing a corrective orthosis comprising:

positioning a subject's ankle and foot in the ankle-foot orthosis of claim 14;

collecting data from the first and second force-torque sensors and the encoder;

analyzing the collected data to determine joint forces of the subject's ankle;

providing means to compensate for a joint force deficiency identified by the data analysis, wherein the means to compensate are proportional to the joint force deficiency.

20. A system for measuring ankle-foot-related forces comprising:

means for positioning a subject's leg and foot in a ankle-foot orthosis, the orthosis including a leg member, a foot member having: (i) a proximal end and a distal end and (ii) a top side and a bottom side, a frame connecting the leg member to the distal end and top side of the foot member, the frame including:

(i) a first frame segment secured to the leg member and extending from the leg member to a first and a second revolute joint, the first and second revolute joints configured and dimensioned to rotate about a first axis, ii) a second frame segment extending from the first and second revolute joints to a third revolute joint, the third revolute joint being positioned: (i) at the distal end of the foot member, and (ii) on the top side of the foot member, the third revolute joint configured and dimensioned to rotate about a second axis, the second axis non-parallel to the first axis, and (iii) a foot member segment secured to the distal end of the foot member and extending to the third revolute joint;

wherein rotation of the first and second revolute joints about the first axis allows the first and second frame segments to rotate with respect to one another;

a first force-torque sensor located on the leg member, a second force-torque sensor located on the foot member, and an encoder positioned on one of the revolute joints;

means for collecting data from the first and second force-torque sensors; and means for analyzing the collected data to determine the motion of the subject's ankle.

* * * * *